United States Patent [19]

Ebmeyer et al.

[11] Patent Number: 5,659,078
[45] Date of Patent: Aug. 19, 1997

[54] PROCESS FOR THE PREPARATION OF TRICHLOROACETYL CHLORIDE

[75] Inventors: Frank Ebmeyer, Augsburg; Tobias Metzenthin, Frankfurt am Main; Günter Siegemund, Hofheim, all of Germany

[73] Assignee: Hoechst Aktiengesellschaft, Germany

[21] Appl. No.: 509,516

[22] Filed: Jul. 31, 1995

[30] Foreign Application Priority Data

Aug. 2, 1994 [DE] Germany .................. 44 27 303.7

[51] Int. Cl.$^6$ ................................ C07C 51/58
[52] U.S. Cl. ........................................ 562/864
[58] Field of Search ............................. 562/864

[56] References Cited

U.S. PATENT DOCUMENTS 1,437,636  12/1922  Dow .
4,643,851  2/1987  Cheminal et al. .

FOREIGN PATENT DOCUMENTS 0 108 675  5/1984  European Pat. Off. .
492175  7/1919  France .

*Primary Examiner*—Paul J. Killos
*Attorney, Agent, or Firm*—Connolly & Hutz

[57] ABSTRACT

The invention relates to a process for the preparation of trichloroacetyl chloride by reaction of acetyl chloride or acetaldehyde or chlorinated derivatives thereof with chlorine in the presence of active charcoal as the catalyst.

8 Claims, No Drawings

PROCESS FOR THE PREPARATION OF TRICHLOROACETYL CHLORIDE

Trichloroacetyl chloride is an important starting substance for the preparation of pharmaceutical and plant protection active compounds.

According to U.S. Pat. No. 3,751,461, trichloroacetyl chloride is obtained by chlorination of acetyl chloride, which can be partly chlorinated, in the liquid phase in the presence of organic nitrogen bases as homogeneous catalysts. This process requires a discontinuous operation of the reactor. It is also necessary for the reaction product to be separated off, by distillation, from the catalyst dissolved therein.

It has now been found, surprisingly, that trichloroacetyl chloride can be prepared by chlorination of acetyl chloride or acetaldehyde or chlorinated derivatives thereof with the aid of active charcoal, that is to say a catalyst which is heterogeneous and can therefore easily be removed.

The invention relates to a process for the preparation of trichloroacetyl chloride by catalytic reaction of acetyl chloride or acetaldehyde, which can be chlorinated, with chlorine, which comprises using active charcoal as the catalyst.

The process is preferably carried out in the manner of customary continuous gas reactions over fixed bed catalysts by passing the gas mixture of organic starting material and chlorine, if appropriate diluted with nitrogen, through a heated reaction tube filled with active charcoal.

The reaction tube is preferably set up vertically and is made of a material which is sufficiently resistant to the reactants.

The process is in general carried out under pressures of $10^{-1}$ to 10 bar, preferably under 1 to 7 bar, in particular under 1 to 5 bar.

The molar ratio of chlorine to the organic starting material is in general regulated such that 1 to 10, preferably 1 to 4, chlorine molecules are present for each hydrogen atom in the starting material.

The reaction is in general carried out at temperatures of from 20° to 300° C., preferably at 100° to 250° C., in particular at 120° to 200° C. A uniform temperature distribution can be achieved by surrounding the reaction tube with a heat transfer liquid.

The conversion of the organic starting material employed is in general complete.

The gas which is formed during the reaction and comprises trichloroacetyl chloride, hydrogen chloride and some chlorine is condensed and worked up by distillation.

The advantages lie in the simplicity of implementation with a heterogeneous catalyst at a very high conversion of organic starting compound.

The organic starting material can also be passed in liquid form over a fixed catalyst bed in the presence of chlorine; this procedure can he realized with continuous or discontinuous operation of the reactor. The reaction here is in general carried out at temperatures of from 20° to 200° C., preferably 80° to 120° C., and under pressures of from 1 to 10 bar, preferably 1 to 7 bar.

The process according to the invention is illustrated in more detail by the following examples. Unless stated otherwise, the conversion reached 100%. The percentage data are molar percentages, unless stated otherwise.

EXAMPLES

A tube of V4A stainless steel of internal diameter 5.0 cm and length 70 cm, which was heated electrically, was used. The internal temperature of the reactor was determined with the aid of an axial thermocouple in a housing. The vertically installed reactor was charged with 1.0 1 (450 g) of commercially available active charcoal (granules), which was heated up slowly in a stream of nitrogen and heated at 300° C. until it released no further water. A stream of 40 g/h of chlorine was then passed over the bulk catalyst at 200° C., and a 40° C. higher "hot spot" was formed which gradually migrated through the bulk catalyst. A catalyst pretreated in this way was used in all the examples.

Example 1

The reaction partners chlorine (purity>99% by weight) and dichloroacetyl chloride (purity>99% by weight) were metered into an evaporator heated at 140° C. upstream of the reactor. Vaporization of the organic component and thorough mixing with the gaseous chlorine took place here. The components were then fed in gaseous form into the reactor, which had been heated to an internal temperature of about 195° C. and filled with the pretreatead catalyst. At a feed of 48 g/h of dichloroacetyl chloride and 41 g/h of chlorine, analysis of the liquid which condensed downstream of the reactor exit gave:

| | |
|---|---|
| Trichloroacetyl chloride: | 98.5% |
| Dichloroacetyl chloride: | 1.0% |
| Carbon tetrachloride: | 0.5% |

Example 2

Chlorine and dichloroacetyl chloride were metered into the reaction apparatus described above. The temperature distribution within the reactor was 200° C. at the hottest point and 180° C. at the coldest point of the bulk catalyst. With metering in of 75 g/h of dichloroacetyl chloride and 63 g/h of chlorine, regular analysis of the liquid condensed downstream of the reactor exit gave:

| | |
|---|---|
| Trichloroacetyl chloride: | 98.0% |
| Dichloroacetyl chloride: | 1.5% |
| Carbon tetrachloride: | 0.5% |

Example 3

24 g/h of acetyl chloride and 79 g/h of chlorine were metered into the reactor described above. The two reaction partners were metered into the evaporator preheated at 60° C. The temperature distribution within the reactor was 225° C. at the hottest point and 190° C. at the coldest point of the bulk catalyst. Regular analysis of the liquid condensed downstream of the reactor during an operating time of 5 h gave the composition:

| | |
|---|---|
| Trichloroacetyl chloride: | 96.6% |
| Dichloroacetyl chloride: | 1.0% |
| Carbon tetrachloride: | 2.4% |

Example 4

16 g/h of acetaldehyde and 130 g/h of chlorine were metered into the reactor described above via the evaporator heated at 60° C. At a temperature distribution between 250°

C. (maximum) and 200° C. (minimum), the reaction gave a liquid product of composition:

| | |
|---|---|
| Trichloroacetyl chloride: | 89.9% |
| Carbon tetrachloride: | 5.5% |
| Chloroform: | 5.6% |

Example 5

39 g/h of trichloroacetaldehyde and 30 g/h of chlorine were metered into the reactor described above via the evaporator heated at 115° C. At a temperature distribution between 250° C. (maximum) and 230° C. (minimum), the reaction gave a liquid product of composition:

| | |
|---|---|
| Trichloroacetyl chloride: | 97.3% |
| Trichloroacetaldehyde: | 1.0% |
| Carbon tetrachloride: | 1.7% |

Example 6

17 g of dried active charcoal (granules) are initially introduced into a 500 ml glass flask, 100 g of dichloroacetyl chloride are added carefully and the mixture is then heated to 110° C., while stirring. 88 g of gaseous chlorine are then passed into the reaction mixture in the course of 3.5 to 4 hours. The chlorination status can be monitored by gas chromatography. After 4.5 hours, the reaction batch is allowed to cool and excess chlorine is driven off by passing in dry air or nitrogen. The active charcoal is then filtered off to give 120 g of trichloroacetyl chloride with a purity of 96%.

We claim:

1. A process for the preparation of trichloroacetyl chloride by catalytic reaction of acetyl chloride or acetaldehyde, which can be chlorinated, with chlorine, which comprises using active charcoal as the catalyst.

2. The process as claimed in claim 1, wherein chloroacetyl chloride is used as the starting material.

3. The process as claimed in claim 1, wherein dichloroacetyl chloride is used as the starting material.

4. The process as claimed in claim 1, wherein chloroacetaldehyde is used as the starting material.

5. The process as claimed in claim 1, wherein dichloroacetaldehyde is used as the starting material.

6. The process as claimed in claim 1, wherein trichloroacetaldehyde is used as the starting material.

7. The process as claimed in claim 1, wherein the reaction is carried out continuously in the gas phase at 100° to 250° C.

8. The process as claimed in claim 1, wherein the molar ratio of chlorine to organic starting material is chosen such that 1 to 4 chlorine molecules are present for each hydrogen atom of the starting material.

* * * * *